(12) United States Patent
Bartenbach et al.

(10) Patent No.: US 12,396,875 B2
(45) Date of Patent: Aug. 26, 2025

(54) BODY SUPPORT DEVICE, THE USE OF IT AND A METHOD OF HANDLING LOADS

(71) Applicant: ETH ZURICH, Zurich (CH)

(72) Inventors: Volker Bartenbach, Uster (CH); Jan Thomas Meyer, Zurich (CH); Rrahim Gashi, Zofingen (CH); Roger Gassert, Wetzikon (CH)

(73) Assignee: ETH ZURICH, Zurich (CH)

( * ) Notice: Subject to any disclaimer, the term of this patent is extended or adjusted under 35 U.S.C. 154(b) by 828 days.

(21) Appl. No.: 17/529,030

(22) Filed: Nov. 17, 2021

(65) Prior Publication Data
US 2022/0071794 A1    Mar. 10, 2022

Related U.S. Application Data

(63) Continuation of application No. PCT/EP2020/063192, filed on May 12, 2020.

(30) Foreign Application Priority Data

May 17, 2019  (EP) ..................................... 19175065

(51) Int. Cl.
*A61F 5/02* (2006.01)
*A61F 5/01* (2006.01)

(52) U.S. Cl.
CPC .............. *A61F 5/026* (2013.01); *A61F 5/028* (2013.01); *A61F 2005/0197* (2013.01)

(58) Field of Classification Search
CPC .. A61F 5/026; A61F 5/028; A61F 5/02; A61F 5/01; A61F 5/0102;
(Continued)

(56) References Cited

U.S. PATENT DOCUMENTS 330,213 A * 11/1885 Deweese ................ A01K 1/04
54/34
9,308,112 B2    4/2016 Kazerooni et al.
(Continued)

FOREIGN PATENT DOCUMENTS

WO    WO2018122106 A1    7/2018
WO    WO2018136722 A1    7/2018

OTHER PUBLICATIONS

International Search Report dated Jul. 28, 2020 in corresponding application dated PCT/EP2020/063192.

*Primary Examiner* — Alireza Nia
*Assistant Examiner* — Daniel A Miller
(74) *Attorney, Agent, or Firm* — McDonald Hopkins LLC (57) ABSTRACT

A body support device to support at least one part of a body when lifting and/or carrying, having at least a first body fastening element fixable above a human's hip joint, at least a second body fastening element mechanically fixable below a human's hip joint and merely on the back side at least one elastic, which mechanically connects the first and the second body fastening element on the back side. The elastic is adapted to be tensioned when a person mechanically linked to the body support device is bending down and to apply an erecting force to the person when the person is bent down. A biasing device adjusts the length of the elastic between the respective fixations on the first body fastening element and the second body fastening element and has a pivotable mounted eccentric element adapted to apply a compressive force on the elastic and a counterpressure surface.

20 Claims, 7 Drawing Sheets

(58) Field of Classification Search
CPC ...... A61F 2005/0197; A61F 2005/0167; A61F
2005/0162; B25J 9/00; B25J 9/0006;
F16D 13/58; A45F 2003/007; A45F
2003/025; A45F 2003/045; A45F
2003/127; A45F 3/00; A45F 3/04; A45F
3/12; A41D 27/26
USPC .......................................................... 602/19
See application file for complete search history.

(56) References Cited

U.S. PATENT DOCUMENTS

| | | | |
|---|---|---|---|
| 2008/0125685 A1* | 5/2008 | Bernardoni | A61F 5/0102 |
| | | | 602/19 |
| 2015/0173993 A1 | 6/2015 | Walsh et al. | |
| 2018/0014961 A1* | 1/2018 | Mylonas | F41H 1/02 |
| 2018/0049905 A1 | 2/2018 | Holscher et al. | |
| 2018/0056104 A1 | 3/2018 | Cromie et al. | |
| 2018/0093374 A1 | 4/2018 | Holgate et al. | |
| 2019/0343707 A1 | 11/2019 | Riener et al. | |
| 2019/0358074 A1* | 11/2019 | Zelik | A61B 5/6811 |
| 2020/0289357 A1* | 9/2020 | Sato | A61H 1/0281 |

* cited by examiner

BODY SUPPORT DEVICE, THE USE OF IT AND A METHOD OF HANDLING LOADS

This nonprovisional application is a continuation of International Application No. PCT/EP2020/063192, which was filed on May 12, 2020, and which claims priority to European Patent Application No. 19175065.2, which was on May 17, 2019, and which are both herein incorporated by reference.

BACKGROUND OF THE INVENTION

Field of the Invention

The present invention relates to a body support device to support at least one part of the human body. In addition, the invention relates to a method of handling loads by a person wearing the body support device and the use of the device.

Description of the Background Art

A wide range of jobs comprises heavy physical labor. Examples are logistics and transport, healthcare, farming or construction. Within a worker's lifetime the fatigue that is associated with physical work can result in illness which is sometimes chronic. Besides the reduction in quality of life for the individual person, this is an economically important factor, because in many cases absence or early retirement due to illness affects the most experienced and highly skilled employees. From this point of view heavy physical work and the resulting illnesses are related to high loss in productivity and injury costs. These problems increase with an aging society.

Within the last years some technical solutions came up to reduce fatigue in physical work or to support persons with physical restrictions due to illness or age.

US2018/0049905A1 and U.S. Pat. No. 9,308,112B2 show devices that are attachable to a person's body to reduce the need of muscle force by using compression springs, gas springs or torque generators. US2018/0056104A1, US2015/0173993A1 and WO2018/122106 show stabilizing exosuits based on multilayer wearables combined with active supporting systems like actuators or motors.

Many of the known solutions, however, have the disadvantage that they are expensive due to their complexity and that the wearing comfort is low for the person using the devices.

SUMMARY OF THE INVENTION

It is therefore an object of the present invention to provide a highly efficient body support device to support at least one part of the human body which supports a person when lifting and/or carrying loads and provides high wearing comfort for the person combined with low costs of producing the device.

A first aspect of the invention is a body support device to support at least one part of the human body, in particular when lifting and/or carrying loads, comprising at least a first body fastening element fixable above a human's hip joint, at least a second body fastening element mechanically fixable below a human's hip joint and merely on the back side at least one elastic which mechanically connects the first and the second body fastening element on the back side of the human body with each other. The elastic is adapted to be tensioned when a person mechanically linked to the body support device is bending down and to apply an erecting force to the person when the person is bent down.

The body support device comprises a biasing device for adjusting the length of the elastic between the respective fixations on the first body fastening element and the second body fastening element. The biasing device comprises a pivotable mounted eccentric element adapted to apply a compressive force on the elastic and a counterpressure surface. The counterpressure surface is arranged essentially perpendicularly to the rotation plane of the eccentric element and is adapted to apply a counter compressive force on the elastic essentially in the opposite direction of the compressive force.

At least in an angular position of the eccentric element, in which the distance between the circumference of the eccentric element and the counterpressure surface is at least the same as the thickness of a portion of the elastic being arranged between the counterpressure surface and the eccentric element, a section of the circumference of the eccentric element facing away from a portion of the elastic that is tensile-loaded or tensile-loadable when a person mechanically linked to the body support device is bending down has a bigger radius than a section of the circumference of the eccentric element facing the portion of the elastic that is tensile-loaded or tensile-loadable mechanically linked to the body support device is bending down.

A person being mechanically linked to the body support device may include that that the person is wearing the device.

The first body fastening element is fixable above the human's hip joint to a person's body by a form fit, in particular via suspenders or straps that are guided over the human shoulder. In one special embodiment the first body fastening element is a wearable vest. The vest may be adaptable to be fit to the individual human torso by adaption elements.

The second body fastening element is fixable below the human's hip joint. In an embodiment the second body fastening element is fixed to at least one human leg and comprises a leg fastening element. In a special embodiment, the second body fastening element comprises at least one adaption element, in particular at least one for each leg adaption element, to fit the second body fastening element to the individual human body.

The elastic is merely located on the back side of the person's body when wearing the said device. This means that the supporting function of the device is essentially exerted when the person is bending down and not when leaning back. Therefore, the device supports the person with an erecting force essentially when the person is bending down or bent down, especially when the person is lifting and/or carrying loads and does not necessarily stabilize the person's body in an upright position in general. In relation to the human body the elastic is in particular essentially located on the back side of the torso.

The elastic mechanically connects the first and the second body fastening element. The connection is a force transmitting connection. When the person is bending down the elastic on the back side of the person wearing the body support device is elastically deformed and tensioned, or in other words stretched. The mechanical force that is transferred to the elastic by the movement of the person bending down results in an erecting restoring force which counteracts the movement. As a consequence, less energy is required from the person's body to stabilize in particular the upper part of the body in the bent position and the person is physically less burdened. The supporting function in this invention is merely realized by the elastic. In other words, the device supports the person wearing it passively. In one embodiment the device does not comprise any active supporting systems or elements like for example actuators or motors and therefore there is no need for regulation and/or control devices and no need for energy supply.

The elastic is adjustable in length by the biasing device. The length of the elastic is according to the invention the distance between the fixation of the elastic at the first fastening element and the second fastening element. The fixation on the first fastening element is realized by the biasing device, in particular by a mechanical force working on the elastic that is clamping the elastic between the eccentric element and the counterpressure surface.

The tensioning force working along the elastic and being induced by a least one tensile portion, which is essentially the portion between the two respective fixations, causes a rotation of the eccentric element so that a section of the circumference of the eccentric element with a bigger radius is moved onto the elastic. Therefore, the distance between the circumference of the eccentric element, in particular the peripheral surface of the eccentric element, and the counterpressure surface is reduced and the compressive force on the elastic is increased. The elastic is clamped between the circumference of the eccentric element and the counterpressure surface and mechanically fixed by friction.

In other words, the biasing device comprises a slit with variable width between the eccentric element and the counterpressure surface wherein the elastic is arranged or arrangeable in the slit and wherein the extension of the slit perpendicular to the longitudinal extension of the elastic is adjustable by a rotation movement of the eccentric element. The tensioning force of the elastic causes a rotation of the eccentric element by friction that narrows the slit and therefore applies a compressive force to the elastic that realizes a fixation of the elastic by frictional engagement.

The counterpressure surface is mechanically fixed to the pivot of the eccentric element in order to maintain a defined distance between the counterpressure surface and the pivot.

The biasing device may comprise a housing that is fixable to the first fastening element by, for example, screws or rivets or another fixation device known to one skilled in the art. The counterpressure surface may form a constructional unit with the housing, as well as a pivot holding the eccentric element.

The biasing device comprises at least one restrictor to guide the elastic at least partially along the moving path of the elastic, in particular at least on the counterpressure surface. The restrictor essentially ensures that the elastic is guided between the circumference of the eccentric element and the counterpressure surface. The restrictor may form a constructional unit with the housing of the biasing device.

The eccentricity of the eccentric element A, which is the distance between the geometric center of the plane of the eccentric element and its pivot, and the diameter of the eccentric element B have a ratio of B/A, wherein B/A is at least 7.

In an example, the ratio of B/A can be at most 10.

The static friction coefficient us between the elastic and the counterpressure surface can be at least 0.3. The static friction coefficient us is the relationship between the forces of friction between two objects that are contacting each other and are both moving in relation to each other in an essentially dry environment.

The counterpressure surface and/or the surface the circumference of the eccentric element can be at least partially roughened and/or comprise surface structure elements in order to increase the frictional engagement.

Additionally, the second body fastening element can comprise a bias to adjust the length of the elastic between the respective fixations on the first body fastening element and the second body fastening element.

In case of two or more elastics, every elastic can comprise at least one biasing device.

The advantage of the biasing device is that the length of the elastic can be adapted to the size of the person wearing it, so that it is ensured that a straight forward inclination of the spine of the person wearing the body support device by at least 5° forward compared to the straight upright or erected position results in a tensile force on the elastic.

The biasing device also allows to adapt the length of the elastic so that it is not supporting the person wearing the body support device. In other words, in this case the device is not active or deactivated.

The biasing device can comprise a deflection member, in particular a pivotable mounted deflection member with a rotation axis perpendicular to the direction of the tensile force of the elastic. The deflection member is adapted to guide the elastic at least partially along the circumference of the eccentric element so that an angle of wrap between the elastic and the eccentric element of at least 10°, in particular of at least 20°, is realized.

In other words, a section of the circumference that corresponds to at least 10° of the rotation plane is essentially in contact with the elastic. The angle of warp is also known as the angle of contact.

The biasing device can comprise at least one sliding element extending essentially perpendicularly to the direction of the tensioning force with a rolling contact bearing to realize a low frictional transport of the elastic. In one embodiment the biasing device comprises several sliding elements to realize an easy movement with low friction of the elastic, in particular while adjusting the length.

The biasing device can comprise a release element that is mechanically connected to the eccentric element and adapted to cause a rotation movement of the eccentric element. Therefore, the distance between the counterpressure surface and the circumference of the eccentric element is increasable so that the elastic is movable between the circumference of the eccentric element and the counterpressure surface.

In other words, the release element may be adapted to revoke the fixation of the elastic caused by frictional engagement between the circumference of the eccentric element and the counterpressure surface.

The slit between the counterpressure surface and the circumference of the eccentric element is expandable by the rotation movement of the eccentric element caused by a movement of the release element so that the compressive force on the elastic is revocable. The elastic is therefore movable through the slit between the counterpressure surface and the circumference of the eccentric element and can therefore be adjusted in length.

The release element is adapted for manual use. In one special embodiment the release element is a lever.

The first body fastening element can comprise at least one stiffening element to increase the buckling resistance of the first body fastening element, in particular to essentially avoid buckling of the first body fastening element caused by compressive stress applied to the first body fastening element by the elastic.

Stiffness in the sense of the invention can mean the resistance of an object against deformation like buckling in response to a supplied compressive stress. In other words, the stiffening element gives the first body fastening element a high buckling resistance. That does not necessarily mean that the stiffening element has a high bending stiffness.

Therefore, the stiffening element is ensuring the fitting of the first body fastening element to the torso of the person mechanically linked to the body support device, in particular when a person mechanically linked to the body support device is moving, in particular is bending down and/or erecting.

The stiffening element may have a modulus of elasticity of at least 1 GPa, in particular 10 GPa.

The stiffening element is may be arranged at least partially in parallel to the direction of the force applied by the elastic on the back side of the human body of a person being mechanically linked to the body support device.

One or more stiffening elements can extend from the clavicle, also known as collarbone, to the lower part of the scapula, also known as shoulder blade, when the body support device is linked to a person. The stiffening element is therefore adapted to fit to a human torso and is at least partially flexible when the person linked to the body support device is bending down or erecting.

The stiffening element can comprise at least one stiff layer like for example a thin metal layer and/or a plastic element. It is also possible that the stiffening element partially comprises different materials. One special embodiment of a stiffness element is a plastic plate with a thickness of 3-5 mm combined with a steel strip with thickness of 0.5-0.7 mm and a width of 20-40 mm, wherein the steel strip is arranged at least partially along a person's shoulder and the plastic plate is arranged in the area of the lower shoulder blade of a person's back, when the person is mechanically linked to the device.

The first fastening element may comprise several layers like a padding layer to realize a comfortable fit to the body of the person linked to the body support device and/or a spacing layer, in particular a breathable spacing mesh material, to support air circulation between the first fastening element body and the body of the person linked to it.

Padding layer and/or spacing layer and/or stiffening element can form a physical unit.

The elastic can have a spring rate between 0.2 N/mm and 6 N/mm, preferably between 0.4 N/mm and 3 N/mm.

The spring rate, which depends on material and design of the elastic, gives the ratio of the acting force of the elastic to the deformation of the elastic, resulting from the distance and/or angle of the movement of a body part of the person wearing the body support device.

The elastic can comprise at least in one section at least one elastic member which is at least one elastic band and/or at least one helical spring.

This includes the possibility that the elastic can be, for example, a helical spring or elastic band. In other words, the elastic is an elastic member and has elastic properties over its whole distance between the first and the second body fastening element. It is also possible that the elastic comprises one or more elastic members only in sections, for example, when the elastic is a strap or a strap system. In this embodiment the connection between the two body fastening elements is realized by at least one strap, in particular a strap made of a webbing material as it is common in backpacking strap systems, which comprises at least one elastic member.

The elastic band can be an essentially flat material having the shape of a stripe but it is also possible that the material is shaped like a rope. It comprises essentially elastic components like latex or natural rubber. Elastic bands are for example known in the field of physiotherapy. It is also possible to arrange several elastic bands as a packet or in layers arranged essentially in parallel or in series to the person's back.

As mentioned above the elastic member can be part of a strap or a strap system. In this embodiment the width of the elastic member may be between 4 cm and 8 cm and the length of the elastic band may be between 8 and 16 cm, wherein width is the horizontal extension and length is the vertical extension referred to an erected human body. The position of the at least one elastic member, referred to this embodiment, is on the back side of a human torso, when the body support device is worn by a person, in particular on the middle third of a human torso.

The elastic can comprise one or more helical springs, for example made of steel.

In general, several elastic members, elastic bands as well as helical springs can be arranged in parallel arrangement and/or serial arrangement in a plane which is essentially parallel to the person's back. A serial arrangement means that for example one elastic comprises two or more elastic members which are arranged one after another along the length extension of the elastic. In other words, one elastic like a strap comprises two or more deformable sections. A parallel arrangement means on the one hand that several elastic comprising at least one elastic member mechanically connect the first and the second body fastening element and that these means are essentially in parallel to each other. On the other hand, a parallel arrangement is given when at least one section of the connection between the first and the second body fastening element comprises several elastic members arranged essentially in parallel to each other.

It is also possible to combine the parallel and serial arrangements. A combination of one or more elastic bands with one or more helical springs is also possible.

The elastic can also have a non-linear spring characteristic.

The spring characteristic may be degressive or progressive. In another example, the elastic can also have a linear spring characteristic.

The spring characteristic describes the correlation between the linear expansion or deformation in length of an elastic, which is in the sense of the invention resulting from the bending movement of the person, and the resulting tensile force, which is in the sense of the invention the erecting force.

With a linear spring characteristic, the erection force and as a result the body supporting effect increases linearly with the deformation or stretching of the elastic. This means that there is only a low erecting force when the person's torso is bent forward only a few degrees, as for example, when the person is carrying a load, and that there is a high erecting force when the person is for example picking up something from the ground.

The advantage of a progressive spring characteristic is that the erecting force, in other words the body supporting effect, increases nonlinearly with the deformation or stretching of the elastic as a result of a bending movement. With respect to the above-mentioned example load carrying is less supported that picking up a weight compared to a linear spring characteristic.

On the opposite, an elastic with a degressive spring characteristic supports carrying loads in a nearly upright position stronger than lifting compared to an elastic with a linear spring characteristic.

The biasing device can be fixed to the first body fastening element in such a manner that the position of the eccentric element is realized on the upper third of a human torso when the first body fastening element is mechanically linked to a person, in particular in such a manner that the position of the eccentric element is in the area of the shoulder of a person.

In other words, the biasing device and therefore the respective fixation of the elastic on the first body fastening element is positioned on a humans' shoulder.

The natural forward bending movement of a person, for example when the person is lifting something from the ground, results in a curvature of the upper spine. In other words, the length extension on the back side on the skin surface in parallel to the spine on the back side of the person in the bended position is increased compared to the erected position. This change in extended length while bending results in a change of length of the elastic. A greater change of length of the elastic, in other words a stronger deformation, results in stronger erecting force to the person wearing the body support device.

The advantage of positioning the fixation on the upper third of the person's torso is that the elastic, in particular the elastic member, is more deformed, implying a stronger erecting force while bending, compared to a force resulting from a lower fixation on the torso.

In an example with two parallel elastic the first fixation on the first body fastening element is realized in the area of the left shoulder blade and the second fixation is realized in the area of the right shoulder blade.

Another advantage of fixing the biasing device on the human shoulder is an easy adjustment of the length of the elastic between the two respective fixations because the eccentric element, in particular the release element connected to the eccentric element, is easy to reach and use by the person wearing the device.

The elastic can comprise a gripper, such as an eyelet, on the end portion that is related to the biasing device. It is also possible that the elastic comprises a gripper on the opposite end portion.

The body support device comprises an intermediate element which is attachable, in particular fixable, to the human body between the first and the second body fastening element. The intermediate element comprises at least one guide member which is adapted to restrict a movement of the elastic essentially perpendicularly to the longitudinal extension of the elastic.

The intermediate element is in particular to be fixed at the human's hip and/or the human's waist. The intermediate element may in one embodiment be a hip and/or waist belt. The intermediate element may comprise an adaption element to fit the intermediate element to the individual body of the person wearing it. The intermediate element comprises at least one guide member. Guide members are for example loops or eyelets. The elastic, which connects the first and the second body fastening element, is guided through the guiding element, for example an eyelet. The function of the guide member is therefore to ensure that the elastic runs essentially in the required orientation even if the person's movement includes rotation of the spine. In other words, the function of the guide member is to avoid that the elastic slides over the hips while the person is moving.

The body support device can comprise at least two elastic which are arrangeable essentially in parallel to the human spine.

In other words, the body support device comprises two elastic which run along the back side of the human body and wherein one elastic is running essentially parallel to the spine at its left side and the other one is running essentially parallel at its right side. The arrangement of the elastic on the back side is particularly essentially axisymmetric to the spine or its straight extension when the person wearing the device is in an erected position. The expression "essentially parallel" also includes an interpolated curved-shaped course with a radius of at least 40 cm. In a parallel arrangement the elastic extend next to each other without overlapping.

More than two elastic are possible, wherein the number of elastics should be even. In case of an odd number of elastic, one of the elastic should extend along the spine.

The body support device can additionally comprise an intermediate element comprising at least one guide member for each elastic, wherein the guide members ensure the essentially parallel arrangement on the back side while the person is moving.

The body support device can comprise at least two elastic which cross each other between the first body fastening element and the second body fastening element.

This means for example that a first elastic is extending from a position of fixation on the person's left shoulder blade to the right leg and the second one from a position of fixation on the person's right shoulder blade to the left leg. The crossing section of the at least two elastic is preferred to be located on the ideal line of the spine, which means that the positions of fixation of the elastic are arranged axisymmetrically to the spine.

The body support device can additionally comprise an intermediate element with one guide member, wherein both elastic of one pair are guided through one guide member. The guide member is in other words the position where the elastic cross.

It is possible that the body support device comprises several pairs of crossing elastic. It is also possible to combine parallel and crossing elastic.

At least one elastic can comprise at least one adjusting device for adjusting the effective length of the elastic member of the elastic.

The effective length of the elastic member is the section of the connection between the first and the second body fastening element that is deformed or stretched by the movement of the person. The effective length affects the erecting force. The shorter the effective length, the higher is the erecting force. Thus, the force applied by the elastic is adjustable by the adjusting device. The advantage of adjusting the effective length is that the supporting effect of the body support device can be adapted to the individual physical condition of the person wearing the device. Also, pretension of the elastic, in particular the elastic member, is possible.

The elastic member can have a non-linear spring characteristic and is mechanically connected to the first body fastening element by a first connector and a second connector and is mechanically connected to the second body fastening element by a third connector or vice versa, wherein the distance between the first and/or the second connector on the one side and the third connector on the other side is adjustable.

"Vice versa" means that is also possible that the first and the second connector are mechanically connected to the second body fastening element and the third connector is mechanically connected to the first body fastening element.

By adjusting the distance between the first and/or the second connector and the third connector the spring rate of the elastic member is adjustable.

The third connector may be a deflector, so that an elastic member like an elastic band is guided from the first connector via the third connector to the second connector. If the distance between the first and the third connector is decreased and the distance between the second and the third connector is simultaneously increased, a higher total spring rate of the elastic member will result in case of a spring with non-linear spring characteristic, in particular for a spring with a progressive spring characteristic. Therefore, in this embodiment adjusting the distance between the first and the second connector results in an adjustment of the tensile force of the elastic member while not changing the total length, in particular the total effective length, of the elastic member.

The second body fastening element comprises a first thigh fastening element and a second thigh fastening element, wherein the first thigh fastening element is adapted to be fixed to the left thigh and the second thigh fastening element is adapted to be fixed to the right thigh.

The thigh fastening elements are for example thigh cuffs. The advantage of fastening the body support device at the thighs of the human body is that in case of a bending movement the distance between the position of fixation on the first body fastening element and the second fastening element along the human back side extends, which results in a stronger deformation of the elastic compared to a higher position on the human body. In particular in combination with the at least one guide member of the intermediate element the fixation of the elastic at the thighs ensures the preferred orientation of the elastic along the back side while the person is moving. Also, it increases wearing comfort compared to other fastening positions below the hip joint.

The thigh fastening elements can comprise adaption elements to fit the cuffs to the individual human leg.

The first body fastening element, the second body fastening element and the intermediate element comprise at least 80% by mass of textile materials in order to minimize weight and volume and increase wearing comfort for the person wearing the body support device.

A textile may be a material essentially made of natural and/or artificial fibers. Besides higher wearing comfort textiles have the advantage to be processed easily.

The body support device can comprise at least one protection element, which prevents at least in sections the contact between the person's back and the elastic.

The advantage of the protection element is to protect the person wearing the said device from being hurt and/or the clothes of the person from being damaged by the elastic, in particular by the elastic member. The protection element is therefore a layer between the person or the clothes and the elastic in order to avoid contact.

The protection element can be a flexible housing that surrounds the elastic or the elastic member, in particular the sections where it is deformed by the person's movement.

The protection element can be a protection plate, which extends over the person's back side between the elastic element and the person's body.

A second aspect of the invention is a method of handling loads, in particular lifting and/or carrying loads, wherein at least one part of a human body of a person being mechanically linked to the body support device according to the invention, in particular wearing the body support device, and lifting and/or carrying loads, is supported by the body support device when the person is bending down or bent down.

A third aspect of the invention is the use of the body support device according to the invention to support at least one part of the human body, when lifting and/or carrying loads.

Further scope of applicability of the present invention will become apparent from the detailed description given hereinafter. However, it should be understood that the detailed description and specific examples, while indicating preferred embodiments of the invention, are given by way of illustration only, since various changes, combinations, and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
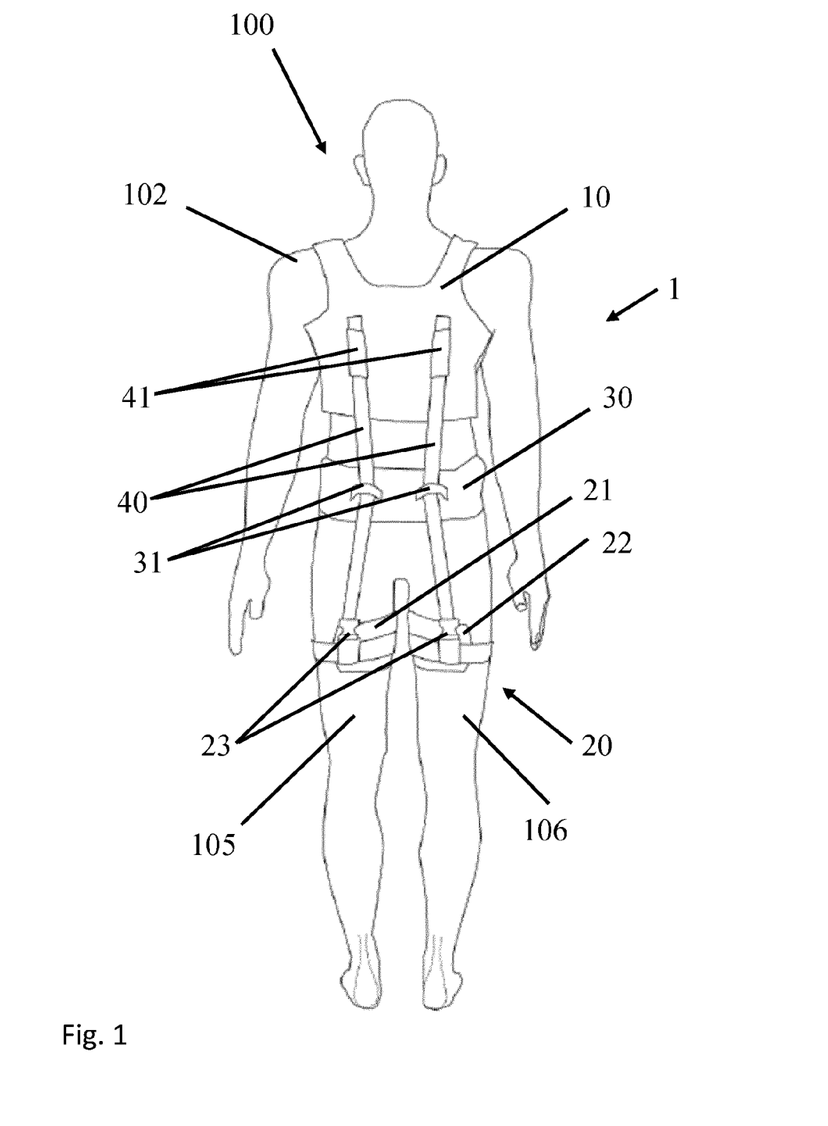
FIG. 1 is a back view of a person wearing an embodiment of the body support device in an erected position.

FIG. 1 shows a back view of a person 100 in an erected position wearing an embodiment of the body support device 1 according to the invention. The body support device 1 shown here comprises a first body fastening element 10 that is executed as a vest to be worn over the shoulders 102, a second body fastening element 20 that is executed as a first thigh fastening element 21 that is linked to the left thigh 105 and a second thigh fastening element 22 that is linked to the right thigh 106. The second body fastening element 20 and the first body fastening element 10 are mechanically connected by two elastic 40 that are arranged essentially parallel to the spine of the person 100 who is wearing the device 1. The elastic 40 are each guided by a guide member 31 that is part of the intermediate element 30. The intermediate element 30 is arranged essentially on the person's hip. Each of the elastic 40 comprises an elastic member 41 which is in the example shown here an elastic band but could also be a spring or spring package. The section of the elastic 40 that is not executed as an elastic band is a strap made of a woven material as it is known for example from backpacks and is less elastic or essentially non-elastic. An embodiment in which the whole elastic 40 is made of an elastic material is also possible.

The elastic 40 are fixed to the thigh fastening elements 21, 22 by thigh fixator 23. In the shown example these thigh fixator 23 are executed as known from backpacks. It is possible that these thigh fixator 23 include the possibility to adjust the length of the elastic 40 between its fixations at the first body fastening element 10 and the fixations at the thigh fastening elements 21, 22.

In the embodiment shown here each elastic 40 comprises only one elastic member 41 which is located between the guide member 31 of the intermediate element 30. This does not exclude embodiments with several elastic members 41, for example arranged in series along the extension of an elastic 40.

The point of fixation on the first fastener 10 of the elastic 40 as shown in this example is in the area of the lower shoulder blades of the person 100.

Figure 2:
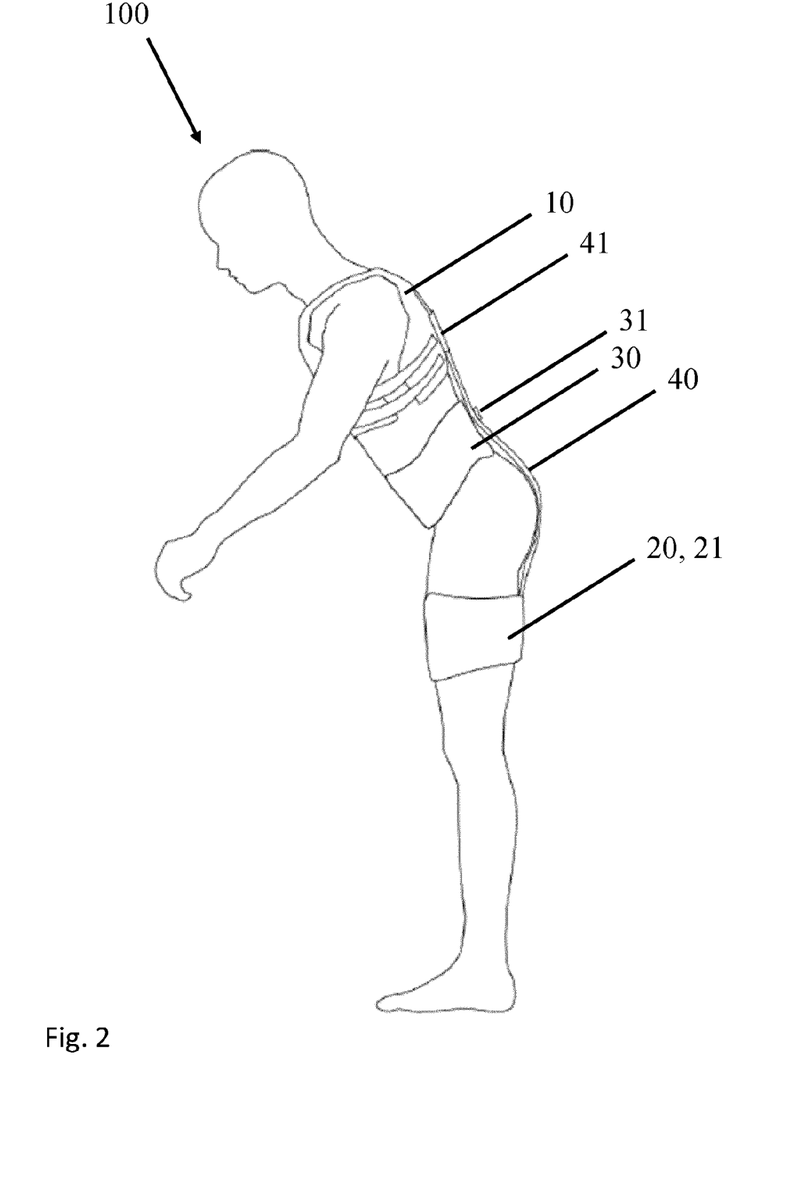
FIG. 2 is a left side view of a person wearing the body support device in a bending position.

FIG. 2 shows the same embodiment of the body support device 1 as FIG. 1 depicting a person 100 in a bending position. When the person 100 is bending down the elastic member 41 of the elastic 40 on the back side of the person 100 wearing the body support device 1 is elastically deformed and tensioned, or in other words stretched. The mechanical force that is transferred to the elastic 40 by the movement of the person 100 bending down results in an erecting restoring force which counteracts the bending movement.

FIG. 2 shows in a left side view that the elastic 40 mechanically connect the first body fastening element 10 and the second body fastening element 20 and that it is guided on the person's back by the guide members 31 arranged on the intermediate element 30.

Figure 3:
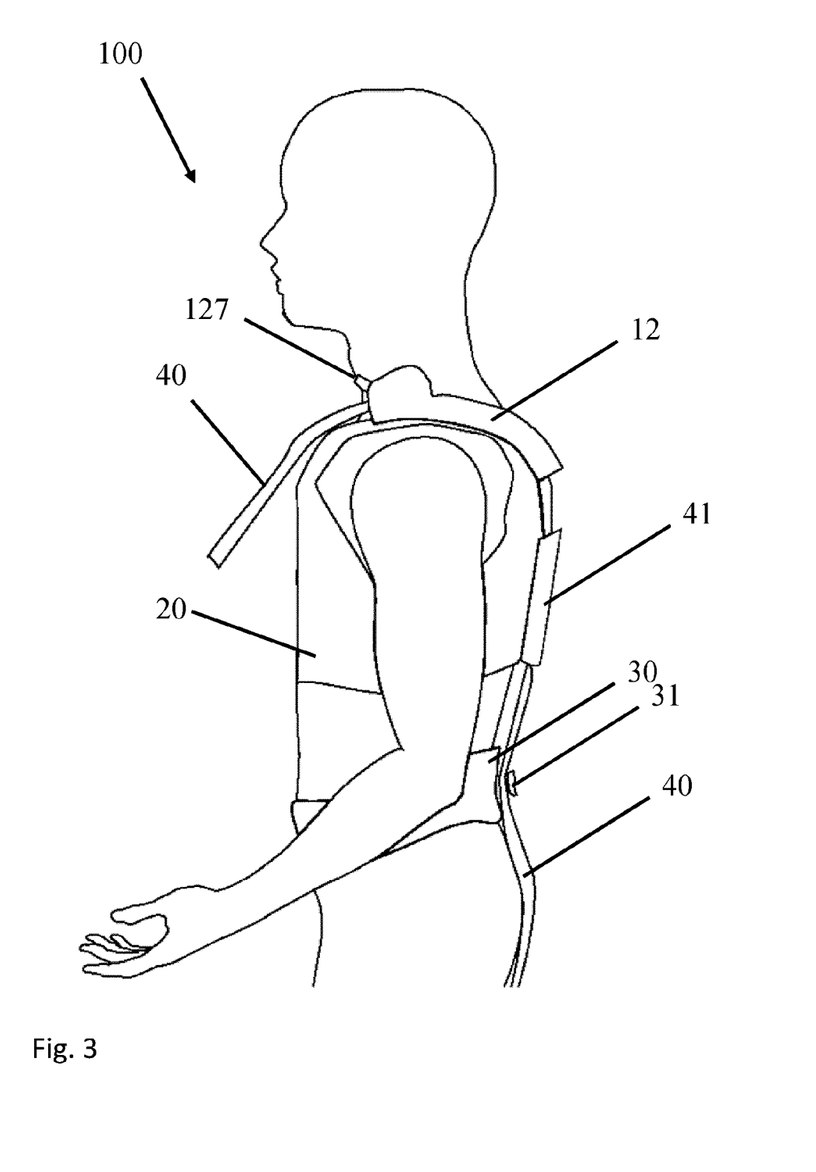
FIG. 3 is a left side view of the upper part of a person wearing the body support device with a biasing device arranged on the shoulder of the person.

FIG. 3 shows a left side view of the upper part of a person 100 wearing an embodiment of the body support device 1. In the embodiment shown here the body support device 1 comprises a biasing device 12 that is fixed at the first body fastening element 10. The elastic 40 that extends essentially on the back of the person's body like shown in FIG. 1 and FIG. 2 is guided through the biasing device 12 so that one end portion of the elastic 40 is located on the front side of the person's body and can easily be reached for adjusting the length of the elastic 40 by the hand of the person 100 while wearing the body support device 1. The biasing device 12 includes the fixation of the elastic 40 on the first body fastening element 10. The portion of the elastic 40 that is related to the back of the person 100 is the tensile-loadable portion comprising the elastic member 41. It can be seen that the elastic member 41 is located between the guide member 31 of the intermediate element 30.

The biasing device 12 comprises a release member 127. The person 100 wearing the body support device 1 can use the release member 127 to revoke the fixation of the elastic 40 that is realized by the biasing device 12. By pulling or releasing the portion of the elastic 40 that is related to the front of the person 100 the length of the elastic 40 is adjustable when wearing the device 1. The portion of the elastic 40 that is related to the front of the person 100 may comprise a gripping element like an eyelet.

Figure 4:
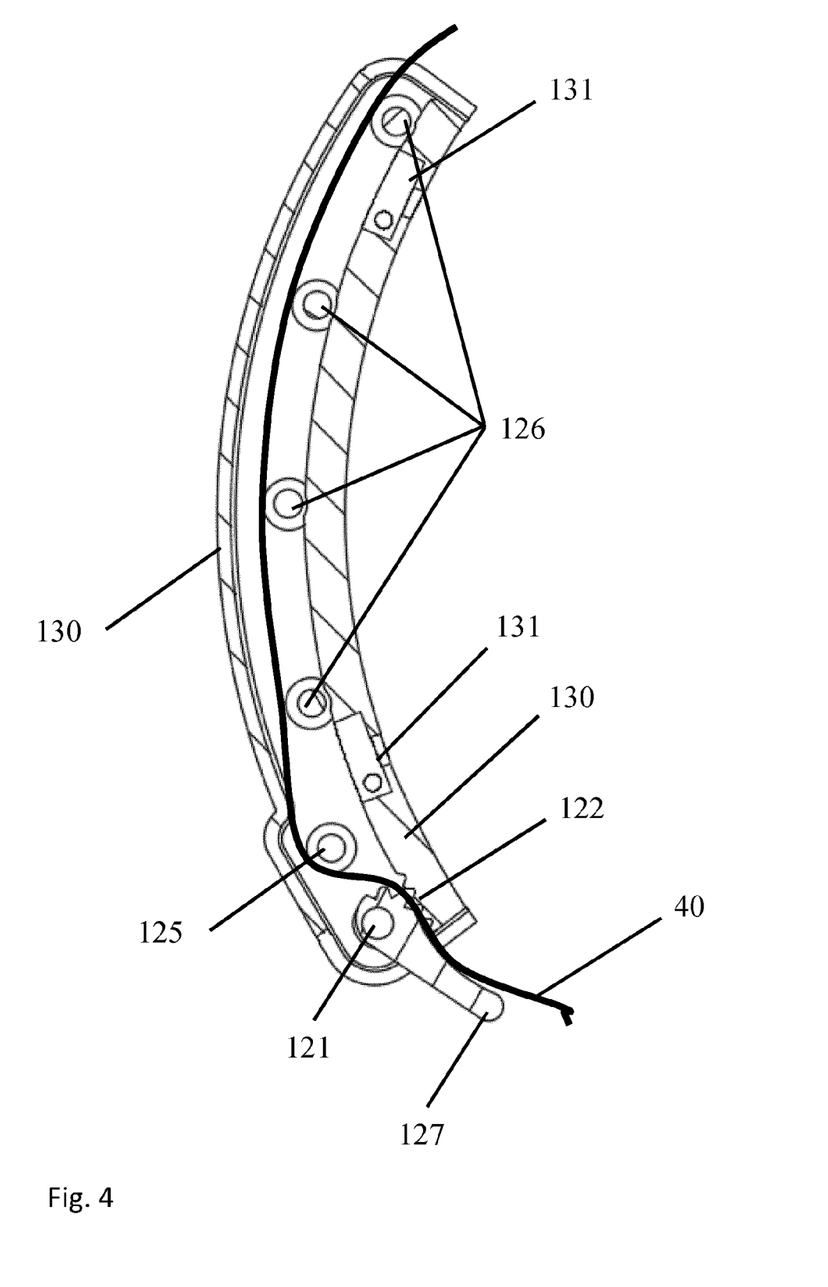
FIG. 4 is a cross-sectional view of an embodiment of the biasing device.

FIG. 4 shows a cross-sectional view of the biasing device 12 and illustrates the function of the biasing device 12. The embodiment of the biasing device 12 shown here is adapted to be fixed on the shoulder portion of the first body fastening element 10 and has therefore a curved form. The concave surface of the housing 130 of the biasing device 12 is adapted to rest on the person's shoulder when the person 100 is mechanically linked to the body support device 1 or at least to the first body fastening element 10.

For fixing the biasing device 12 on the first body fastening element 10 the biasing device 12 comprises two biasing device fixator 131 being part of the housing 130. The biasing device fixator 131 are adapted to fix the biasing device 12 to the body fastening element 10 via screws or similar components.

The elastic 40 is guided from the person's back side through the housing 130 of the biasing device 12 over the person's shoulder to the person's front side. Therefore, in the embodiment shown here the biasing device 12 comprises four sliding elements 126. In this special embodiment the sliding elements 126 are executed as rolling contact bearings to realize a low frictional transport of the elastic 40. A similar effect can also be achieved by using a sliding surface. The advantage of the sliding elements 126 is to realize an easy movement with low friction of the elastic 40 while adjusting its length.

The fixation and therefore the adjustment in length is realized by an eccentric element 121 and a counterpressure surface 122. The eccentric element 121 and the counterpressure surface 122 realize a slit through which the elastic 40 is guided. The width of the slit perpendicular to the extension in length of the elastic 40 is adjustable by a rotation movement of the eccentric element 121 which is mounted pivotable. The tensile force of the elastic 40, in particular the elastic member 41, is causing a first rotation movement of the eccentric element 121 by friction that narrows the slit. This effect is supported by the deflection member 125 that is in the given example mounted pivotable, too. The deflection member 125 guides the elastic 40 between the circumference of the eccentric element 121 and the counterpressure surface 122, in other words into the slit, so that an angle of wrap on the circumference of the eccentric element 121 of at least 10° is realized. The higher the angle of warp the less tensile force of the elastic 40 is needed to cause the first rotation movement of the eccentric element 121. Furthermore, the biasing device 12 comprises a release element 127 that is mechanically connected to the eccentric element 121. In the embodiment shown here the eccentric element 121 and the release element 127 constitute a physical unit. The release element 127 is adapted to cause a second rotation movement opposite to the first rotation movement when being used by a person 100 to widen the slit between the eccentric element 121 and the counterpressure surface 122 so that the fixation of the elastic 40 is revoked and the elastic 40 is movable through the biasing device 12 for adjusting its length. FIG. 4 shows that the surface of the circumference of the eccentric element 121 and the counterpressure surface 122 comprise elevations like teeth of a gearwheel. This additionally increases the friction and therefore the fixation of the elastic 40.

Figure 5:
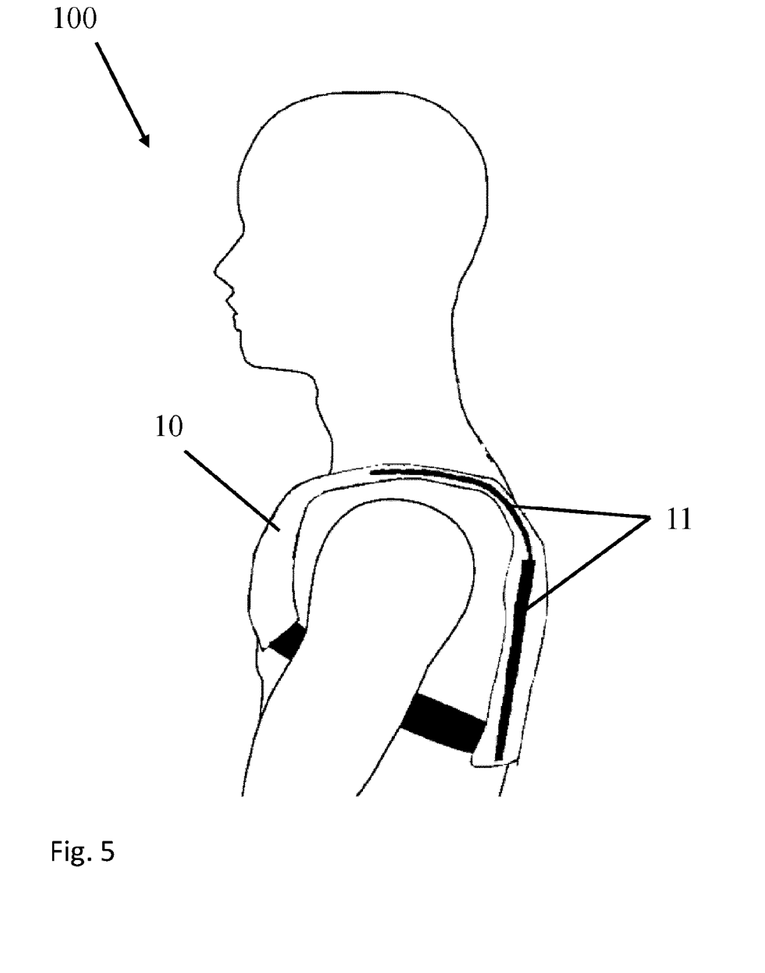
FIG. 5 is a left side view of the upper part of a person wearing a body support device with stiffening elements.

FIG. 5 shows a left side view of the upper part of a person 100 wearing a body support device 1 with at least one stiffening element 11. In the embodiment shown here the stiffening element 11 is embedded in the first body fastening element 10 and comprises two portions. The lower portion that is arranged in the area of the shoulder blade is in this special embodiment a plastic plate. The upper portion arranged over the shoulder of the person 100 is a steel band. The advantage of the embedded stiffening element 11 is that it increases the buckling resistance of the first body fastening element 10 caused by compressive stress applied to the first body fastening element 10 by the elastic 40. The compressive stress is in particular applied when the person 100 is erecting. The stiffening element 11 causes a good fit to the person's torso in particular when the person 100 is moving. The plastic plate and the steel band are flexible enough that the bending movement of the person 100 being mechanically linked to the device 1 is not restricted.

Figure 6A:
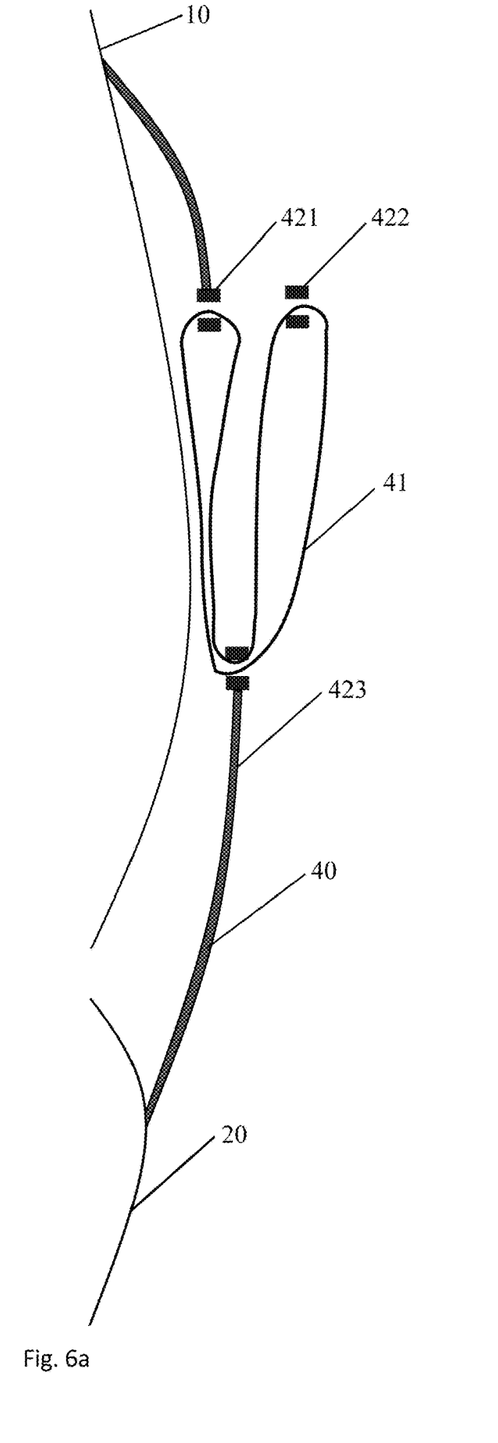
FIG. 6a is a first position of adjustment of the elastic member.
Figure 6B:
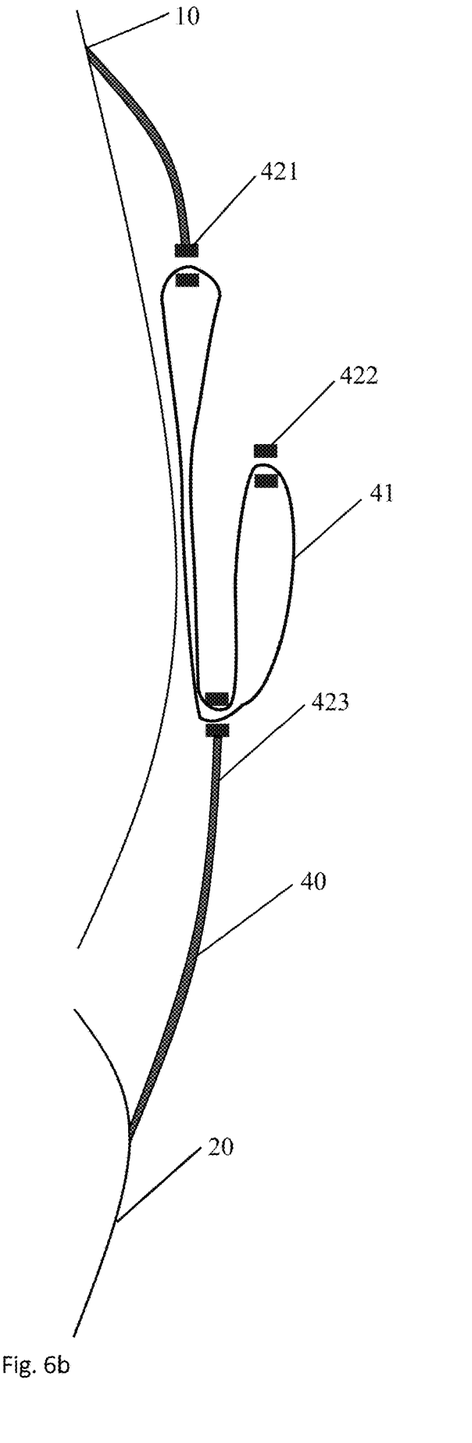
FIG. 6b is a second position of adjustment of the elastic member.

FIG. 6a shows a first position and FIG. 6b shows a second position of adjustment of the elastic member 41 which is in the given example an elastic band, in particular a closed loop of an elastic material with a non-linear spring characteristic. FIG. 6a and FIG. 6b illustrate the principle of adjusting the total spring rate of the elastic member 41.

The elastic member 41 is mounted or hooked to the first connector 421 and a second connector 422. Both connector 421, 422 are mechanically connected to the first body fastening element 10. The elastic member 41 is deflected by the third connector 423 which is mechanically connected to the second body fastening element 20. In FIG. 6*a* the distance in the direction of the tensile force of the elastic member 41 between the first connector 421 and the second connector 422 is essentially zero. In other words, the elastic member 41 has two sections of nearly the same length. The elastic member 41 is working as two parallel springs of the same length and the same spring rate.

FIG. 6*b* shows an increased distance between the first connector 421 and the second connector 422 which results in two sections of the elastic member 41 with different length. In this case the elastic member 41 is working as two parallel springs of different length and the same spring rate. Because the elastic band has a non-linear, in particular progressive, spring characteristic the total spring rate of the arrangement shown in FIG. 6*b* is different compared to the one in the arrangement shown in FIG. 6*a*. In the given example of an elastic band with a progressive spring characteristic the total spring rate of the arrangement shown in FIG. 6*b* is higher than the one in FIG. 6*a* while the total length of the elastic member 41 has not changed.

Figure 7:
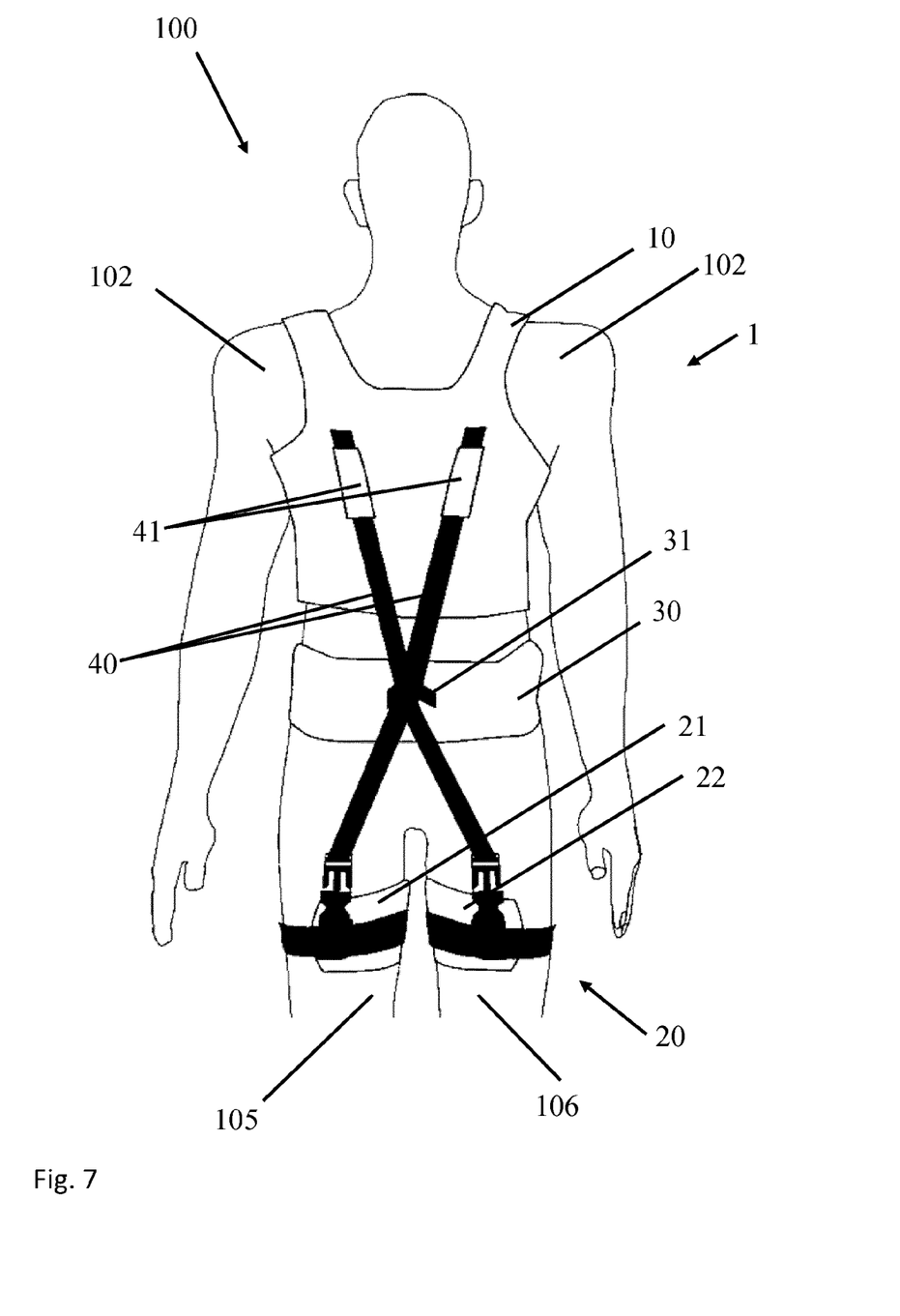
FIG. 7 is a back view of a person wearing an embodiment of the body support device in an erected position with two crossed elastic.

FIG. 7 shows a back view of a person 100 wearing another embodiment of the body support device 1 in an erected position with two crossed elastic 40. The body support device 1 shown here comprises essentially the same elements as the body support device 1 shown in FIG. 1. Basically, the body support device 1 comprises a first body fastening element 10 executed as a vest that is mechanically connected to the second body fastening element 20 which comprises a first and a second thigh fastener 21, 22 by two elastic 40 each comprising an elastic member 41. The main difference is that the intermediate element 30 has only one guide member 31 to guide both elastic 40 wherein the elastic 40 are crossed. That means that one of the elastic 40 is connected to the first body fastening element 10 in the area of the right shoulder and extends to the left thigh 105 while the other one extends vice versa to the right thigh 106.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A body support device configured to support at least one part of a human body when lifting and/or carrying loads, the body support device comprising:
   at least a first body fastener configured to be fixable above a human's hip joint;
   at least a second body fastener configured to be mechanically fixable below the human's hip joint and on a back side;
   at least one elastic that mechanically connects the first body fastener and the second body fastener configured to be on the back side of the human body with each other, the at least one elastic being adapted to be tensioned when a user mechanically linked to the body support device is bending down and to apply an erecting force to the user when the user is bent down; and
   a biasing device to adjust a length of the at least one elastic between the respective fixations on the first body fastener and the second body fastener and wherein the biasing device comprises a pivotable mounted eccentric element adapted to apply a compressive force on the at least one elastic and a counterpressure surface, wherein the counterpressure surface is arranged essentially perpendicularly to a rotation plane of the pivotable mounted eccentric element and is adapted to apply a counter compressive force on the at least one elastic essentially in an opposite direction of the compressive force, and
   wherein at least in an angular position of the pivotable mounted eccentric element in which a distance between a circumference of the pivotable mounted eccentric element and the counterpressure surface is at least the same as a thickness of a portion of the at least one elastic being arranged between the counterpressure surface and the eccentric element; wherein the pivotable mounted eccentric element has a first radius and a second radius, wherein the first radius is larger than the second radius, and the pivotable mounted eccentric element is arranged so that when the user bends down the tensile force of the at least one elastic causes the pivotable mounted eccentric element to undergo a rotational movement into an orientation in which the first, larger, radius extends substantially towards the counterpressure surface so that the at least one elastic is clamped between the pivotable mounted eccentric element and counterpressure surface.

2. The body support device configured to support the at least one part of the human body according to claim 1, wherein the biasing device comprises a deflection member or a pivotable mounted deflection member with a rotation axis substantially perpendicular to a direction of the tensile force of the at least one elastic that is adapted to guide the at least one elastic at least partially along the circumference of the pivotable mounted eccentric element so that an angle of wrap between the at least one elastic and the pivotable mounted eccentric element of at least 10° or of at least 20° is realized so as to reduce the amount of tensile force of the at least one elastic required to cause the rotational movement of the eccentric element.

3. The body support device configured to support the at least one part of the human body according to claim 2 wherein as the angle of wrap increases, a level of tensile force required to cause the rotation movement of the pivotable mounted eccentric element decreases.

4. The body support device configured to support the at least one part of the human body according to claim 1, wherein the at least one elastic has a non-linear spring characteristic.

5. The body support device configured to support the at least one part of the human body according to claim 4, wherein the at least one elastic is mechanically connected to the first body fastener by a first connector and a second connector and is mechanically connected to the second body fastener by a third connector or vice versa, and wherein a distance between the first connector and/or the second connector a first side and the third connector is adjustable.

6. The body support device configured to support the at least one part of the human body according to claim 1, wherein the pivotable mounted eccentric element and the counterpressure surface define a slit through which the at least one elastic is guided; and wherein the rotational movement of the pivotable mounted eccentric element, caused by the tensile force of the at least one elastic, narrows a width of the slit.

7. The body support device configured to support the at least one part of the human body according to claim 6, wherein the width of the slit is perpendicular to the length of the at least one elastic.

8. The body support device configured to support the at least one part of the human body according to claim 1, wherein the biasing device comprises a release element mechanically connected to the pivotable mounted eccentric element and adapted to cause the rotational movement of the eccentric element, wherein the distance between the counterpressure surface and the circumference of the pivotable mounted eccentric element is increasable so that the at least one elastic is movable between the circumference of the pivotable mounted eccentric element and the counterpressure surface.

9. The body support device configured to support the at least one part of the human body according to claim 1, wherein the first body fastening element comprises at least one stiffening element to increase a buckling resistance of the first body fastening element or to essentially avoid buckling of the first body fastening element caused by compressive stress applied to the first body fastening element by the at least one elastic.

10. The body support device configured to support the at least one part of the human body according to claim 1, wherein the at least one elastic comprises, at least in one section, at least one elastic member which is at least one elastic band and/or at least one helical spring.

11. The body support device configured to support the at least one part of the human body according to claim 1, wherein the biasing device is configured to be fixed to the first body fastener in such a manner that the position of the pivotable mounted eccentric element is realized on the upper third of a human torso when the first body fastener is mechanically linked to the user such that the position of the pivotable mounted eccentric element is configured to be in an area of a shoulder of the user.

12. The body support device configured to support the at least one part of the human body according to claim 1, wherein the body support device comprises an intermediate element which is configured to be attachable or fixable to the human body between the first body fastener and the second body fastener, and which comprises at least one guide member, which is adapted to restrict a movement of the at least one elastic essentially perpendicularly to the longitudinal extension of the at least one elastic.

13. The body support device configured to support the at least one part of the human body according to claim 1, wherein the at least one elastic comprises at least two elastics which are arrangeable essentially in parallel to a spine of the user when the user is mechanically linked to the body support device.

14. The body support device configured to support the at least one part of the human body according to claim 1, wherein the body support device comprises at least two elastics which cross each other between the first body fastener and the second body fastener.

15. The body support device configured to support the at least one part of the human body according to claim 1, wherein the at least one elastic comprises at least one adjuster to adjust an effective length of the at least one elastic.

16. The body support device configured to support the at least one part of the human body according to claim 1, wherein the second body fastener comprises a first thigh fastening element and a second thigh fastening element, wherein the first thigh fastening element is adapted to be fixed to a left thigh and the second thigh fastening element is adapted to be fixed to a right thigh.

17. A method of handling loads, the method comprising:
mechanically linking at least one part of a human body of a user to a body support device as claimed in claim 1; and
supporting, when lifting and/or carrying loads, by the body support device when the user is bending down or bent down.

18. A body support device according to claim 1 further comprising
a deflection member which is arranged to guide the at least one elastic between the circumference of the pivotable mounted eccentric element and the counterpressure surface, so that an angle of wrap, which is greater than 0°, is formed between the at least one elastic and the circumference of the eccentric element, so as to reduce the amount of tensile force of the at least one elastic required to cause the rotational movement of the eccentric element.

19. The body support device according to claim 1, wherein the pivotable mounted eccentric element is selectively moveable to a position in which the second radius extends substantially towards the counterpressure surface, so that the at least one elastic is free to move between the pivotable mounted eccentric element and counterpressure surface.

20. A body support device configured to support at least one part of a human body when lifting and/or carrying loads, the body support device comprising:
at least a first body fastener configured to be fixable above a human's hip joint;
at least a second body fastener configured to be mechanically fixable below the human's hip joint and on a back side;
at least one elastic that mechanically connects the first body fastener and the second body fastener configured to be on the back side of the human body with each other, the at least one elastic being adapted to be tensioned when a user mechanically linked to the body support device is bending down and to apply an erecting force to the user when the user is bent down; and
a biasing device to adjust a length of the at least one elastic between the respective fixations on the first body fastener and the second body fastener and wherein the biasing device comprises a pivotable mounted eccentric element adapted to apply a compressive force on the at least one elastic and a counterpressure surface, wherein the counterpressure surface is arranged essentially perpendicularly to a rotation plane of the pivotable mounted eccentric element and is adapted to apply a counter compressive force on the at least one elastic essentially in an opposite direction of the compressive force, and wherein at least in an angular position of the pivotable mounted eccentric element in which a distance between a circumference of the pivotable mounted eccentric element and the counterpressure surface is at least the same as a thickness of a portion of the at least one elastic being arranged between the counterpressure surface and the eccentric element, a section of the circumference of the eccentric element facing away from a portion of the at least one elastic that is tensile-loaded or tensile-loadable when the user mechanically linked to the body support device is bending down has a bigger radius than a section of the circumference of the eccentric element facing the portion of the at least one elastic that is tensile-loaded or tensile-loadable when the user mechanically linked to the body support device is bending down, so that the tensile force of the at least one elastic will cause a rotational movement of the eccentric element.

\* \* \* \* \*